(12) United States Patent
Hintz et al.

(10) Patent No.: US 8,349,614 B2
(45) Date of Patent: Jan. 8, 2013

(54) ALKALINITY DETERMINATION

(75) Inventors: Christopher Hintz, Wilmington Island, GA (US); Kenneth J. Hintz, Fairfax Station, VA (US)

(73) Assignees: George Mason Intellectual Properties, Inc., Fairfax, VA (US); University of South Carolina, Columbia, SC (US)

( * ) Notice: Subject to any disclaimer, the term of this patent is extended or adjusted under 35 U.S.C. 154(b) by 177 days.

(21) Appl. No.: 12/707,529

(22) Filed: Feb. 17, 2010

(65) Prior Publication Data
US 2010/0210026 A1 Aug. 19, 2010

Related U.S. Application Data

(60) Provisional application No. 61/153,137, filed on Feb. 17, 2009.

(51) Int. Cl.
| | |
|---|---|
| G01N 31/18 | (2006.01) |
| G01N 31/00 | (2006.01) |
| G01N 25/00 | (2006.01) |
| G01N 25/20 | (2006.01) |
| G01N 31/16 | (2006.01) |

(52) U.S. Cl. ............. 436/147; 436/163; 422/75; 422/77
(58) Field of Classification Search .................. 436/147; 422/75, 77
See application file for complete search history.

(56) References Cited

U.S. PATENT DOCUMENTS
2007/0178595 A1* 8/2007 Raghuraman et al. .......... 436/43

OTHER PUBLICATIONS
SOP 3, Determination of total alkalinity in sea water, Version 2.11, Aug. 6, 1997, pp. 1-30.*

* cited by examiner

Primary Examiner — Christine T Mui
(74) Attorney, Agent, or Firm — Edgar Rodriguez

(57) ABSTRACT

Alkalinity determination, including an alkalinity determination process and/or alkalinity determinator. An alkalinity determination process may include providing a known value of volume of an acidic fluid, forming a titration system by providing one or more additions of a known value of volume of a relatively alkaline fluid to an acidic fluid, determining a pH value and/or a temperature value for one or more additions and/or determining an alkalinity value of a system by calculating a transformation including one or more determined pH values and/or temperature values of one or more additions. An alkalinity determination process may include modeling, such that an informed determination may be made with reference to relevant and/or irrelevant factors, as well as parameters to maximize likelihood of alkalinity determination. In embodiments, an alkalinity determinator may include one or more titration cells, one or more sensors and/or one or more alkalinity value determinators.

23 Claims, 10 Drawing Sheets

| Beginning $V_i$ mL | Accuracy / Precision Response | | Ending pH | Accuracy / Precision Response | |
|---|---|---|---|---|---|
| | Normalized | at 0.62 mM HCl mM | | Normalized | at 0.62 mM HCl mM |
| 0.0 | 1.0000 ± 0.0015 | 0.6200 ± 0.0009 | 3.0 | 0.9992 ± 0.0043 | 0.6195 ± 0.0027 |
| 0.1 | 0.9999 ± 0.0016 | 0.6199 ± 0.0010 | 3.1 | 0.9998 ± 0.0023 | 0.6199 ± 0.0014 |
| 0.2 | 1.0000 ± 0.0017 | 0.6200 ± 0.0011 | 3.2 | 1.0000 ± 0.0017 | 0.6200 ± 0.0011 |
| 0.3 | 1.0001 ± 0.0018 | 0.6201 ± 0.0011 | 3.3 | 1.0000 ± 0.0015 | 0.6200 ± 0.0009 |
| 0.4 | 1.0001 ± 0.0019 | 0.6201 ± 0.0012 | 3.4 | 0.9999 ± 0.0013 | 0.6199 ± 0.0008 |
| 0.5 | 1.0001 ± 0.0023 | 0.6201 ± 0.0014 | 3.5 | 0.9997 ± 0.0012 | 0.6198 ± 0.0007 |
| | | | 3.6 | 0.9996 ± 0.0011 | 0.6198 ± 0.0007 |
| | | | 3.7 | 0.9994 ± 0.0011 | 0.6196 ± 0.0007 |

FIG. 9

ALKALINITY DETERMINATION

CROSS-REFERENCE TO RELATED APPLICATIONS

This application claims the benefit of U.S. Provisional Application No. 61/153,137, filed Feb. 17, 2009, entitled "An Alternative Small-Volume, Precise Total Alkalinity Measurement for Seawater by Reverse Gran Titration," which is hereby incorporated by reference in its entirety.

REFERENCE TO COMPUTER PROGRAM LISTINGS

A portion of the present disclosure is contained in a computer program listing appendix filed electronically herewith as an ASCII text file, which is hereby incorporated by reference in its entirety. The ASCII text file is entitled Listing.txt created on Feb. 17, 2010 of approximately 964 kilobytes.

DESCRIPTION OF THE DRAWINGS

Example

Example

Example

Example

Example

Example

Example

Example

Example FIG. 9 is a table illustrating an alkalinity determination process in accordance with embodiments.

DESCRIPTION OF THE EMBODIMENTS

According to embodiments, Reverse Gran (RG) titration may be used to determine alkalinity, including total alkalinity. Alkalinity may relate to a value used to determine constituent concentrations in a sample, for example constituent concentration of a carbonate system such as $[CO_2^*]$, $[HCO_3^-]$ and/or $[CO_3^{2-}]$. Constituent concentrations may reside in a fluid, for example a carbonate system may reside in a sample of seawater.

According to embodiments, alkalinity determination may achieve maximized precision and/or accuracy. In embodiments, alkalinity determination may use minimized sample size. In embodiments, alkalinity determination may not require accurate and/or frequent calibration of an acid. In embodiments, time to complete alkalinity determination may be minimized. In embodiments, alkalinity determination may not require a priori knowledge of total constituents.

Figure 1:
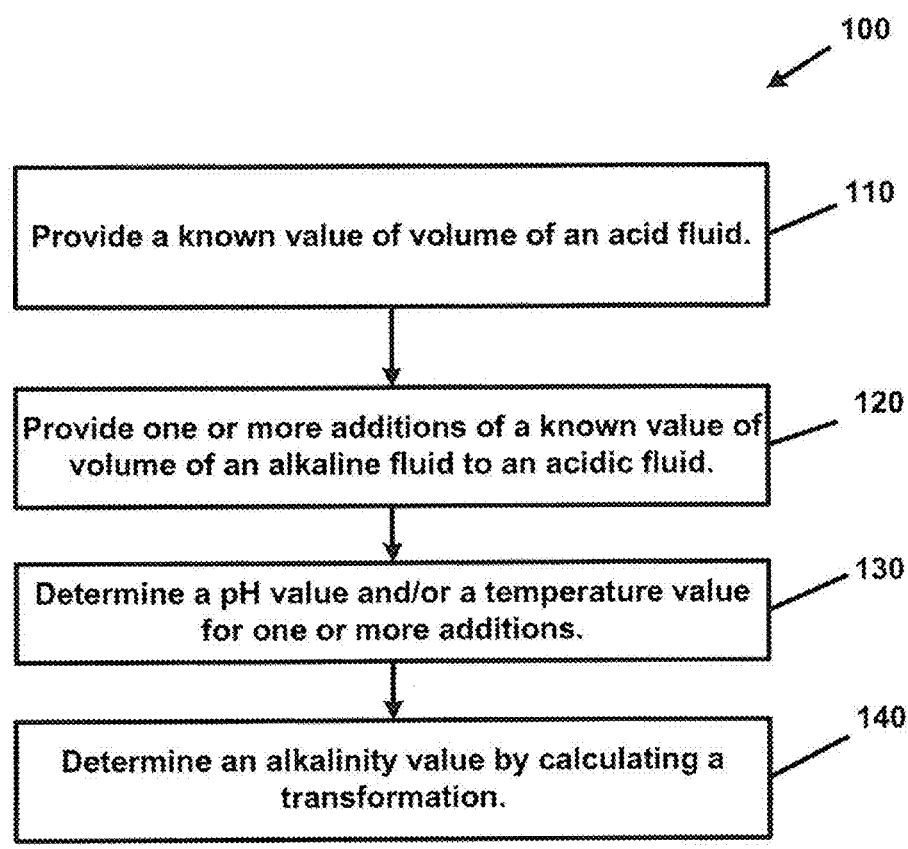
FIG. 1 illustrates an alkalinity determination process in accordance with embodiments.

Referring to example FIG. 1, alkalinity determination process 100 in accordance with one aspect of embodiments may include providing a known value of volume of an acidic fluid 110. According to embodiments, an acidic fluid may be any fluid having a pH of approximately 7 or less. In embodiments, an acidic fluid may include HCl. In embodiments, a value of volume of acidic fluid may be known by providing a preselected amount of acidic fluid. In embodiments, a value of volume of acidic fluid may be known by adding acidic fluid and measuring the added amount to determine a known amount.

According to embodiments, an alkalinity determination process may include forming a titration system by providing one or more additions of a known value of volume of a relatively alkaline fluid to the acidic fluid 120. In embodiments, an alkaline fluid may be any fluid having a pH of approximately 7 or more, for example when an acidic fluid provided has a pH of approximately 7 or less. In embodiments, alkaline fluid may include seawater, waste water, ground water, agricultural water, recreational water, industrial water, and/or drinking water. In embodiments, alkaline fluid may include other forms, including biological fluids such as blood. In embodiments, a value of volume of alkaline fluid may be known by providing a preselected amount of alkaline fluid. In embodiments, a value of volume of alkaline fluid may be known by adding alkaline fluid and measuring the added amount to determine a known amount.

According to embodiments, seawater may relate to water from a sea and/or ocean, or to a composition simulating seawater. In embodiments, waste water may relate to any water affected by anthropogenic influence, such as sewage water. In embodiments ground water may relate to liquid water flowing through shallow aquifers, soil moisture, permafrost, immobile water in bedrock, deep geothermal and/or oil formation water. In embodiments, agricultural water may relate to water used in the production of food and/or goods, for example through farming and/or forestry. In embodiments, recreational water may relate to water for fish tanks, personal aquariums, pools, jacuzzis, lakes and/or rivers. In embodiments, industrial water may relate to municipal aquariums, pools, and/or water used by a manufacturing facility for fabricating, processing, washing, diluting, cooling, and/or transporting a product, incorporating water into a product, and/or for sanitation needs. In embodiments, drinking water may relate to any water that is consumed.

According to embodiments, an alkalinity determination process may include determining a pH value and/or a temperature value for one or more additions of alkaline fluid to acidic fluid 130. In embodiments, a pH value may relate to hydrogen ion concentration/activity. In embodiments, a pH value and a temperature value may be determined by measuring pH and temperature of a titration system using a pH sensor and a temperature sensor, respectively, which may be housed together and/or separately in one or more sensors. In embodiments, measuring a pH and/or a temperature value may occur for each addition of alkaline fluid to acidic fluid, and/or for a subset of additions including a single addition. In embodiments, mixing may be provided prior, during and/or subsequent to one or more additions of alkaline fluid to acidic fluid such that determining a pH and/or temperature value may also include mixing.

According to embodiments, an alkalinity determination process may include determining an alkalinity value of a titration system by calculating a transformation 140. In embodiments, a transformation may be calculated using a determined pH value and/or temperature value of one or more additions of alkaline fluid to acidic fluid. In embodiments, a transformation may be calculated for each addition of alkaline fluid to acidic fluid, and/or for a subset of additions including a single addition.

Figure 2:
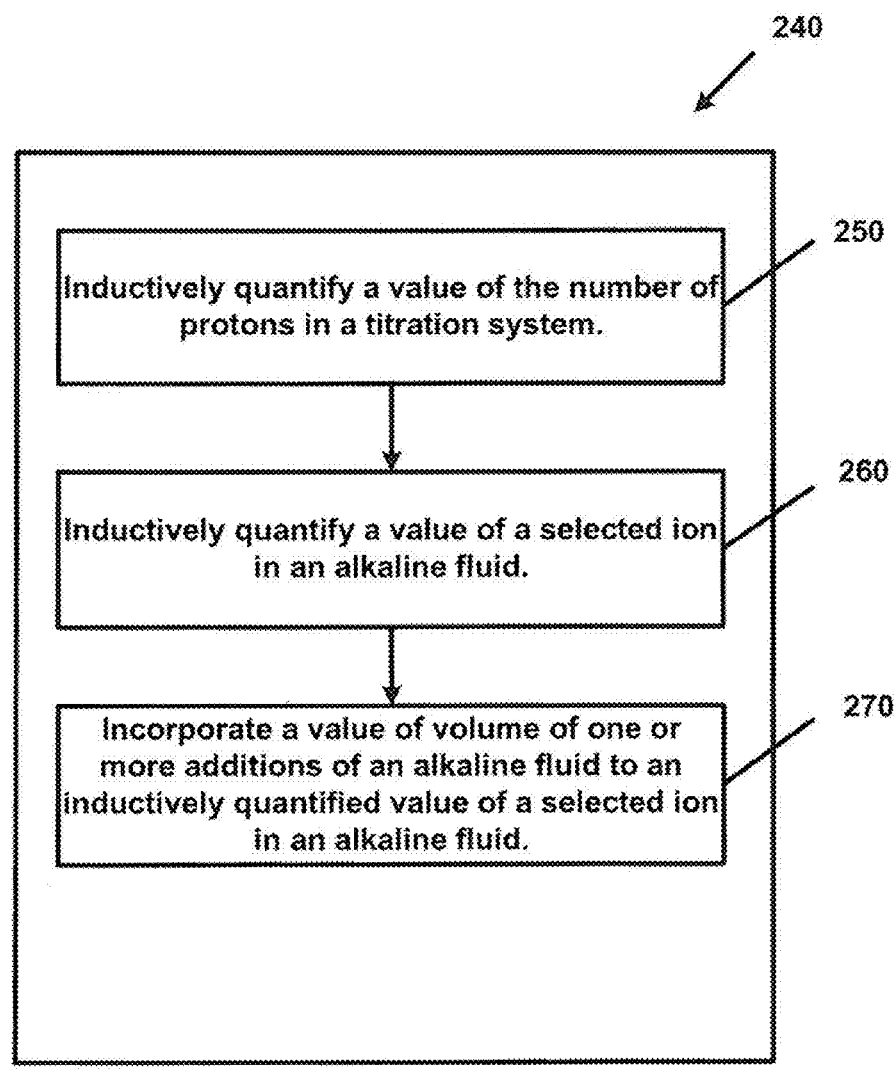
FIG. 2 illustrates an alkalinity determination process in accordance with embodiments.

Referring to example FIG. 2, alkalinity determination process 200 in accordance with one aspect of embodiments including calculating a transformation 240 may inductively quantify a value of the number of protons in a titration system

250. According to embodiments, inductive quantification may relate to quantification using logical reasoning and/or formula. In embodiments, the number of protons in a titration system may be inductively quantified using example equation (1) as follows:

$$pH = -\log [H^+] \quad (1)$$

In embodiments, for example when an electrode is used to measure pH, the number of protons in a titration system may be inductively quantified using example equation (2) as follows:

$$E = E^\circ + \frac{RT}{zF}[H^+] \quad (2)$$

where E is the cell potential, $E^\circ$ is the standard cell potential, R is the universal gas constant, T is the temperature, z is the number of electrons transferred, and F is the Faraday constant.

According to embodiments, calculating a transformation may include an inductively quantified value of a selected ion in the alkaline fluid 260. In embodiments, an inductively quantified value may be determined for each addition of alkaline fluid to acidic fluid, and/or for a subset of additions including a single addition.

According to embodiments, for example when an alkaline fluid includes seawater, a value of a selected ion in the alkaline fluid may be inductively quantified using one or more of example equations (3) to (21) as follows:

$$C_T = [CO_2^*] + [HCO_3^-] + [CO_3^{2-}] \quad (3)$$

$$B_T = [B(OH_3)] + [B(OH)_4^-] \quad (4)$$

$$S_T = [HSO_4^-] + [SO_4^{2-}] \quad (5)$$

$$F_T = [HF] + [F^-] \quad (6)$$

$$P_T = [H_3PO_4] + [H_2PO_4^-] + [HOP_4^{2-}] + [PO_4^{3-}] \quad (7)$$

$$Si_T = [Si(OH)_4] + [SiO(OH)_3^-] \quad (8)$$

$$[HCO_3^-] = \frac{C_T K_{1C}[H^+]}{[H^+]^2 + K_{1C}[H^+] + K_{1C}K_{2C}} \quad (9)$$

$$[CO_3^{2-}] = \frac{C_T K_{1C} K_{2C}}{[H^+]^2 + K_{1C}[H^+] + K_{1C}K_{2C}} \quad (10)$$

$$[B(OH)_4^-] = \frac{B_T}{1 + [H^+]/K_B} \quad (11)$$

$$[OH^-] = K_W/[H^+] \quad (12)$$

$$[H_3PO_4] = \frac{P_T[H^+]^3}{[H^+]^3 + K_{1P}[H^+]^2 + K_{1P}K_{2P}[H^+] + K_{1P}K_{2P}K_{3P}} \quad (13)$$

$$[H_2PO_4^-] = \frac{P_T K_{1P}[H^+]^2}{[H^+]^3 + K_{1P}[H^+]^2 + K_{1P}K_{2P}[H^+] + K_{1P}K_{2P}K_{3P}} \quad (14)$$

$$[HPO_4^{2-}] = \frac{P_T K_{1P} K_{2P}[H^+]}{[H^+]^3 + K_{1P}[H^+]^2 + K_{1P}K_{2P}[H^+] + K_{1P}K_{2P}K_{3P}} \quad (15)$$

$$[PO_4^{3-}] = \frac{P_T K_{1P} K_{2P} K_{3P}}{[H^+]^3 + K_{1P}[H^+]^2 + K_{1P}K_{2P}[H^+] + K_{1P}K_{2P}K_{3P}} \quad (16)$$

$$[SiO(OH)_3^-] = \frac{Si_T}{1 + [H^+]/K_{Si}} \quad (17)$$

$$[HSO_4^-] = \frac{S_T}{1 + K_S/[H^+]_F} \quad (18)$$

$$[H^+]_F = [H^+]/Z \quad (19)$$

$$Z = 1 + S_T/K_S \quad (20)$$

$$[HF] = \frac{F_T}{1 + K_F/[H^+]} \quad (21)$$

where $C_T$ references total carbon, $B_T$ references total is total boron, $S_T$ references total sulfur, $F_T$ references total fluorine, $P_T$ references total phosphorous, $Si_T$ references total silica, S references salinity, Z references a factor that relates fee-hydrogen proton concentration to standard proton concentration, and the equilibrium constants K for the acid/base system are $K_{1C}$, $K_{2C}$, $K_B$, $K_W$, $K_{1P}$, $K_{2P}$, $K_{3P}$, $K_{Si}$, $K_S$, $K_F$.

According to embodiments, any suitable stoichiometric model may be utilized to inductively quantify components of one or more chemical reactions of interest. In embodiments, substantially all and/or a subset of substantially all components of a reaction may be inductively quantified. In embodiments, for example when an alkaline fluid added to an acidic fluid is seawater, a selected ion may include one or more of a hydrogen ion, a hydrogen sulfate ion, a hydrogen fluoride ion, a bicarbonate ion, a trihydrogen phosphate ion and/or a hydrogen phosphate ion.

According to embodiments, calculating a transformation may include incorporating a value of volume of an addition, of alkaline fluid to acidic fluid, to an inductively quantified value of a selected ion in an added alkaline fluid 270. In embodiments, for example when an alkaline fluid added to an acidic fluid includes seawater, a transformation may be calculated using one or more of example equations (22)-(25) as follows, which may be used together with at least equations (1) to (21):

$$F_2 = (V_i + V_o)[H^+]_i + V_i([HSO_4^-]_{SW} + [HF]_{SW} - [HCO_3^-]_{SW}) \quad (22)$$

$$H_2 = (V_i + V_o)[H^+]_i + V_i([HSO_4^-]_{sw} + [HF]_{sw})$$

$$I_2 = (V_i + V_o)[H^+]_i + V_i([HSO_4^-]_{sw} + [HF]_{sw} + [H_3PO_4]_{sw} - [HCO_3^-]_{sw} - [H_3PO_4^{2-}]_{sw})$$

where $F_2$, $H_2$ and $I_2$ reference embodiment mass balances of selected components including a value of volume of an addition Vi, the added alkaline fluid, to $V_O$, the volume of acidic fluid prior to each of one or more additions, such that $V_i+V_O$ reference total volume from one or more additions. Subscript i references a total, such that $[H^+]_i$ references total proton concentration of the system. Subscript SW denotes selected components of the added alkaline fluid, for example seawater.

According to embodiments, an alkalinity value may be determined by a calculating a transformation which may incorporate a value of volume of an addition to an inductively quantified value of a selected ion using, in one aspect of embodiments, one or more of example equations (25)-(27) as follows, which may be used together with at least equations (1) to (24):

$$\frac{dF_2}{dV} = [H^+]_{sw} + [HSO_4^-]_{sw} + [HF]_{sw} - [HCO_3^-]_{sw} \quad (25)$$

$$\frac{dH_2}{dV} = [H^+]_{sw} + [HSO_4^-]_{sw} + [HF]_{sw} \quad (26)$$

$$\frac{dI_2}{dV} = [H^+]_{sw} + [HSO_4^-]_{sw} + [HF]_{sw} + [H_3PO_4]_{sw} - [HCO_3^-]_{sw} - [H_3PO_4^{2-}]_{sw} \quad (27)$$

Figure 3:
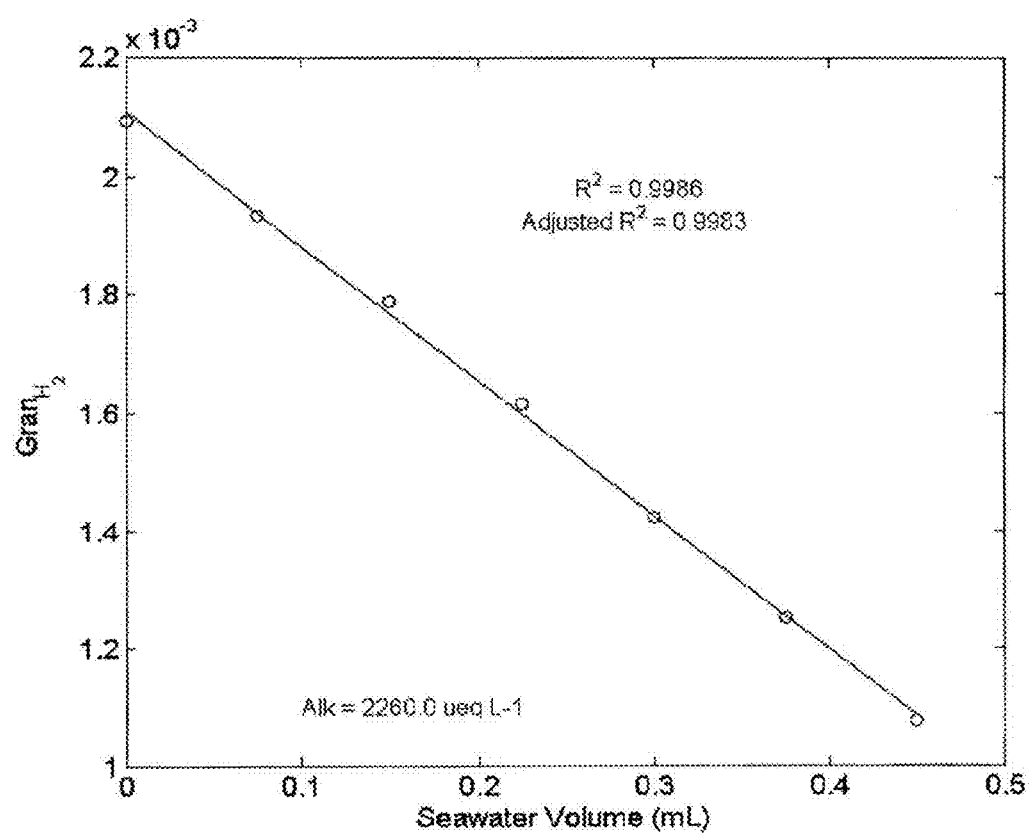
FIG. 3 is a graph illustrating an alkalinity determination process in accordance with embodiments.

According to embodiments, without being bound to any particular theory, added alkalinity may be substantially completely neutralized in excess acid yielding a determinable and/or measurable change in alkaline fluid pH which may represent added charge to a titration system. In embodiments, as described at least by equations (25) to (27) in one aspect of embodiments of alkalinity determination, a first order least-squares regression of a mass balance with respect to volume may yield a slope which may include an unexpected and superior determinable alkalinity value of an alkaline fluid sample. Referring to example FIG. 3, one aspect of embodiments of alkalinity determination is illustrated in graph form. In embodiments, acid concentration may be neglected and/or may be unnecessary.

According to embodiments, a selected component may be preselected in accordance with any suitable criteria. In embodiments, for example, a component may be preselected based on modeled parameters, as described herein. In another aspect of embodiments, a selected component may be preselected by neglecting non-selected components, for example based on trivial concentrations at particular pH ranges. In embodiments, for example, $P_T$, $Si_T$ and other constituents may be neglected and/or selected constituents may be preselected as described in one aspect of embodiments in equations (22) and/or (25) in accordance with a pH range between approximately 3.2 and 4.5. In embodiments, for example, $[HCO_3]$ may be neglected based on negligible concentrations as described in one aspect of embodiments in equations (23) and/or (26) in accordance with a pH range below approximately 3.2.

According to embodiments, selected components may be preselected in accordance with source of a sample. In embodiments, for example, $C_T$ may be selected in accordance with oxic oceanic seawater conditions, as described in one aspect of embodiments in equations (22) and/or (25), and/or $P_T$ may be selected in accordance with nutrient rich costal waters as described in one aspect of embodiments in equations (28) and/or (32). According to embodiments, selected components may be preselected to include substantially all components in a system.

According to embodiments, selected components may be preselected in accordance with mixing. In embodiments, for example when the alkaline fluid includes seawater, selected components may be preselected based on the presence and/or absence of conservative mixing between proton donors and acceptors. In embodiments, for example, equilibrium coefficients may be different during initial alkaline fluid additions to acidic fluid while total acid/base concentrations may be conservative and/or total alkalinity may be conserved. In embodiments, a transformation may be calculated in accordance with mixing using one or more of example equations (28)-(32) as follows:

$$F_{2i} = (V_i + V_O)\left( [H^+]_i + \frac{S_{Ti}}{1 + \frac{K_S}{[H^+]_{Fi}}} + \frac{F_{Ti}}{1 + \frac{K_F}{[H^+]}} - \frac{C_{Ti} K_{1C}[H^+]}{[H^+]^2 + K_{1C}[H^+] + K_{1C}K_{2C}} \right) \quad (28)$$

$$F_{2i} = (V_i + V_O)\left( [H^+]_i + \frac{S_{Ti}[H^+]_{Fi}}{[H^+]_{Fi} + K_F} + \frac{F_{Ti}[H^+]_i}{[H^+]_i + K_F} - \frac{C_{Ti} K_{1C}[H^+]_i}{[H^+]_i^2 + K_{1C}[H^+]_i + K_{1C}K_{2C}} \right) \quad (29)$$

$$F_{2i} = (V_i + V_O)[H^+]_i + \left( \frac{V_i S_{Tsw}[H^+]_{Fi}}{[H^+]_{Fi} + K_F} + \frac{V_i F_{Tsw}[H^+]_i}{[H^+]_i + K_F} - \frac{V_i C_{Tsw} K_{1C}[H^+]_i}{[H^+]_i^2 + K_{1C}[H^+]_i + K_{1C}K_{2C}} \right) \quad (30)$$

$$F_{2i} = (V_i + V_O) \quad (31)$$

$$\left( [H^+]_i + \left(\frac{V_i}{V_i + V_O}\right)\frac{S_{Tsw}[H^+]_{Fi}}{[H^+]_{Fi} + K_F} + \left(\frac{V_i}{V_i + V_O}\right)\frac{F_{Tsw}[H^+]_i}{[H^+]_i + K_F} - \left(\frac{V_i}{V_i + V_O}\right)\frac{C_{Tsw} K_{1C}[H^+]_i}{[H^+]_i^2 + K_{1C}[H^+]_i + K_{1C}K_{2C}} \right)$$

where $$[H^+]_{Fi} = \frac{[H^+]_i K_S}{K_S + \left(\frac{V_i}{(V_i + V_o)}\right)S_{Tsw}} \quad (32)$$

According to embodiments, alkalinity determination may include using an acid concentration value $C_a$. In embodiments, for example, $C_a$ may be inductively quantified using one or more of example equations (25)-(27). In embodiments, for example using a first titration subset of data between an initial acidic fluid value $V_o$ without sample to a first predetermined condition, such as pH, temperature and/or volume, $C_a$ may be inductively quantified by plotting a first-order polynomial least-squares regression using one or more of example equations (25)-(27) and dividing the y-intercept of the relation by $V_o$.

According to embodiments, alkalinity determination may include using a second titration subset of data from a first predetermined condition of a first titration subset to a second predetermined condition of a second subset. In embodiments, for example, alkalinity determination may include using a first-order polynomial least-squares regression including one or more of example equations (25)-(27) and a fixed boundary condition which may include C. In embodiments, a fixed boundary condition may be inductively quantified using example equation (33):

$$C_a \times V_o \quad (33)$$

According to embodiments, alkalinity determination may include any suitable device and/or system configured to determine any suitable factor, for example to measure temperature, pH and/or volume. In embodiments, suitable devices and/or systems may be portable and/or stationary. In embodiments, samples may be added while an alkalinity determinator is mobile and/or is stationary. In embodiments, for example, alkalinity determination may utilize electrochemical and/or spectrophotometric operations. In embodiments, an electrochemical operation may reference a chemical reaction that occurs between an electron conductor, for example metal or semiconductor, and an ionic conductor, for example an electrolyte. In embodiments, a spectrophotometric operation may reference determination of a structure and/or characteristic of a substance, such as pH, by measuring a capacity to absorb light at one or more wavelengths.

Figure 4:
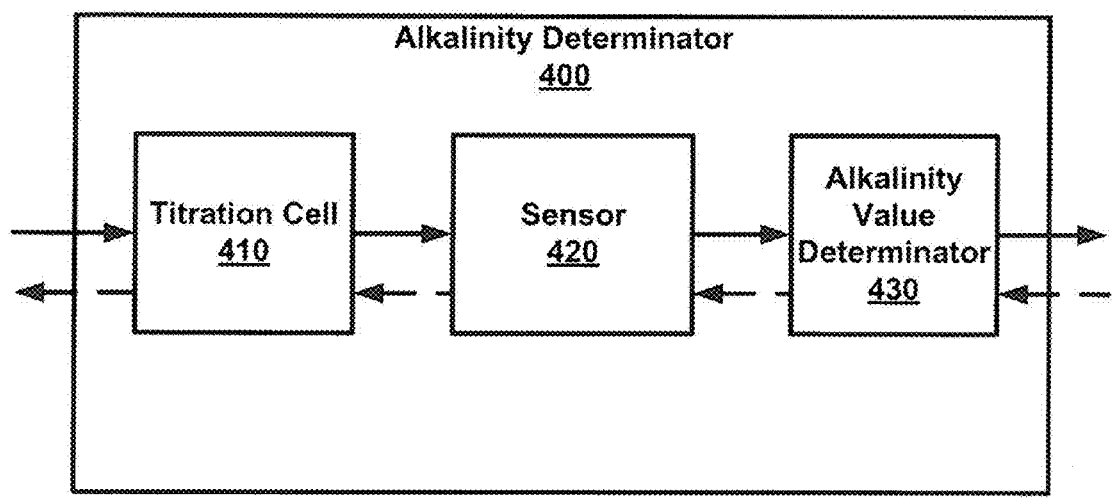
FIG. 4 illustrates an alkalinity determinator in accordance with embodiments.

Referring to example FIG. 4, alkalinity determinator 400 in accordance with one aspect of embodiments is illustrated. According to embodiments, alkalinity determinator 400 may include one or more of a titration cell 410, sensor 420 and/or alkalinity value determinator 430. In embodiments, titration cell 410 may be configured to house a titration system including an acidic fluid and one or more added known values of volumes of a relatively alkaline fluid to the acidic fluid.

According to embodiments, sensor 420 may be configured to determine one or more pH values of a system for one or more additions of an added known value of volume, including a provided acidic fluid and/or an added alkaline fluid. In embodiments, sensor 420 may be configured to determine one or more temperature values for one or more additions of an added known value of volume, including a provided acidic fluid and/or an added alkaline fluid. In embodiments, sensor 420 may be configured to determine one or more absorbance values for one or more additions of an added known value of volume, including a provided acidic fluid, a reagent and/or an added alkaline fluid.

According to embodiments, alkalinity value determinator 430 may be configured to determine an alkalinity value. In embodiments, alkalinity value determinator 430 may be configured to determine an alkalinity value by calculating a transformation including one or more determined values. In embodiments, a determined value may include a determined pH value, a determined temperature value and/or a determined absorbance value.

Figure 5:
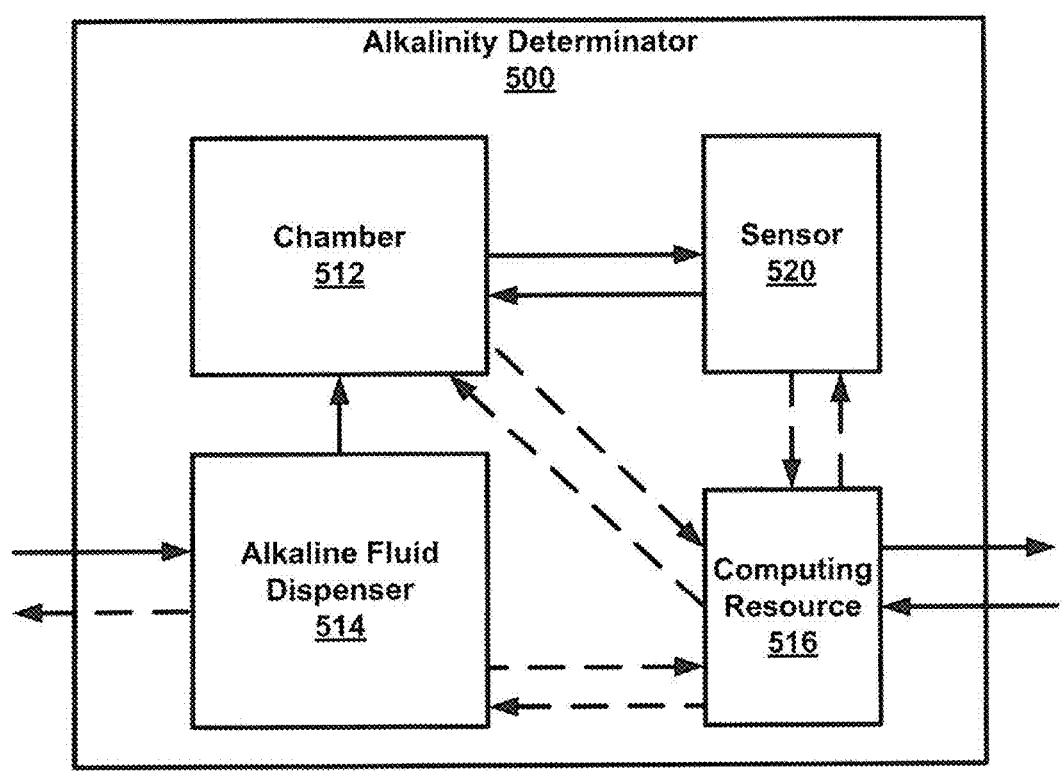
FIG. 5 illustrates an alkalinity determinator in accordance with embodiments.

Referring to example FIG. 5, alkalinity determinator 500 may include chamber 512, which may form part of titration cell 510. In embodiments, chamber 512 may be configured to house one or more acidic fluids. In embodiments, chamber 512 may be in communication with parts of alkalinity determinator 500, for example sensor 520 and/or alkaline fluid dispenser 514. In embodiments, communication may reference fluid, mechanical, electrical and/or data communication.

According to embodiments, alkalinity determinator 500 may include one or more alkaline fluid dispensers 514. In embodiments, alkaline fluid dispensers 514 may be in communication with chamber 512. In embodiments, alkaline fluid dispenser 514 may include a buret. In embodiments, a buret may include one or more pumps and/or valves which may operate to dispense fluid. In embodiments, alkaline fluid dispenser 514 may include a pipetter. In embodiments, a burett and/or a pipetter may be configured to be managed by an electronic controller and/or a force, such as pressure.

According to embodiments, alkalinity determinator 500 may include computing resource 516. As illustrated in one aspect of embodiments in FIG. 5, computing resource 516 may be in communication with titration cell 510, alkalinity fluid dispenser 514 and/or sensor 520. In embodiments, computing resource 516 may house an alkalinity value determinator and/or may be in communication with an alkalinity value determinator that is distributively located relative to one or more parts of alkalinity determinator 500. In embodiments, computing resource may be configured to implement one or more of a storing data operation, a processing data operation and an outputting data operation.

Figure 6:
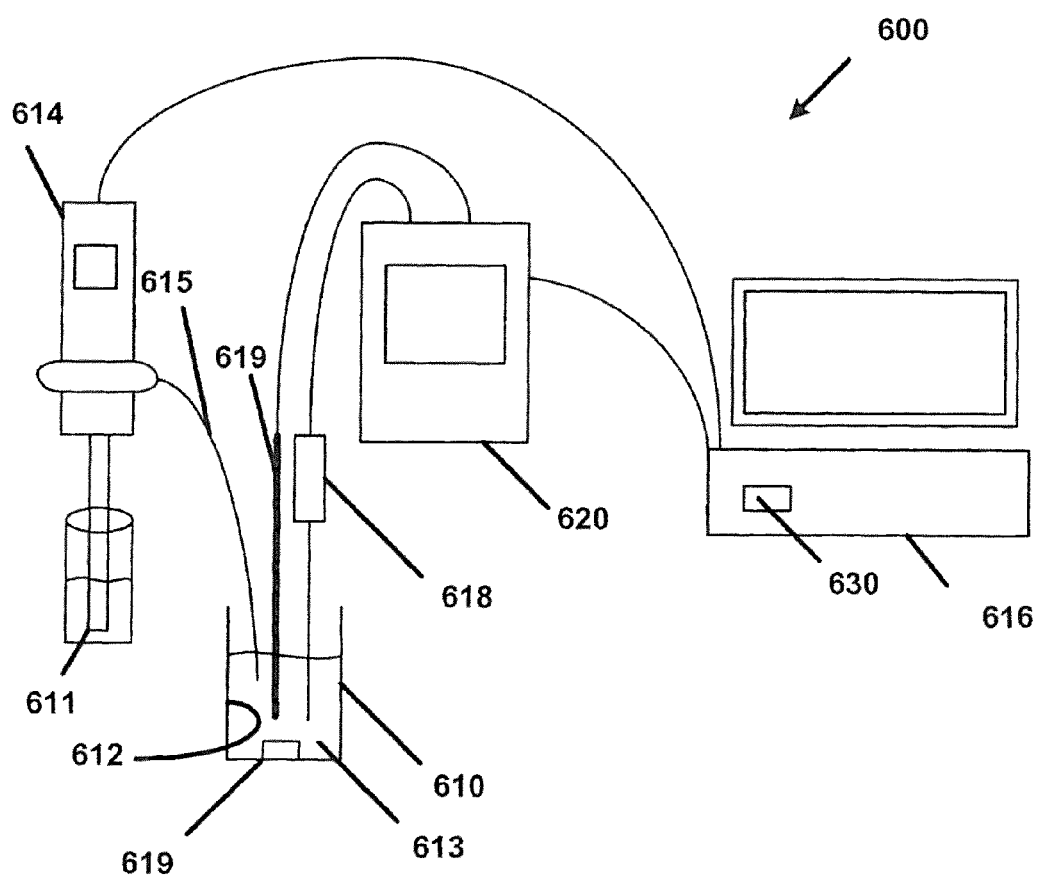
FIG. 6 illustrates an alkalinity determinator in accordance with embodiments.

Referring to example FIG. 6, alkalinity determinator 600 may include one or more of a titration cell 610, sensor 620 and/or alkalinity value determinator 630. In embodiments, titration cell 610 may include chamber 612, which may be exposed to ambient conditions and/or may house one or more acidic fluids 613. In embodiments, chamber 612 may be in communication with sensor 620, for example through pH probe 618 and/or temperature probe 619. In embodiments, alkalinity determinator 600 may include one or more alkaline fluid dispensers 614, which may be configured to supply alkaline fluid 611 and/or may include a digital buret configured to be managed, for example, by an electronic controller. In embodiments, alkaline fluid dispenser 614 may be in communication with chamber 612, for example through conduit 615.

According to embodiments, mixing may be achieved by any suitable operation, including providing a jet and/or a stirbar in titration cell 610, applying a force to a sidewall of titration cell 610 and/or by inducing and/or allowing motion for titration cell 610. In embodiments, mixing may be accomplished prior, during and/or after one or more additions of alkaline fluid.

According to embodiments, alkalinity value determinator 630 may be configured to determine an alkalinity value by calculating a transformation including one or more determined values. In embodiments, alkalinity value determinator 630 may be configured to utilize a determined pH value and/or a determined temperature value. In embodiments, a determined amount may include a predetermined amount and/or a measured amount. In embodiments, alkalinity value determinator 630 may reside in computing resource 616. In embodiments, computing resource 616 may be in communication with titration cell 610, alkalinity fluid dispenser 614 and/or sensor 620. In embodiments, a computing resource may be configured for wired data communication, for example Ethernet communication, and/or wireless data communication, for example USB, Bluetooth, Satellite, WiFi, and/or Firewire.

Figure 7:
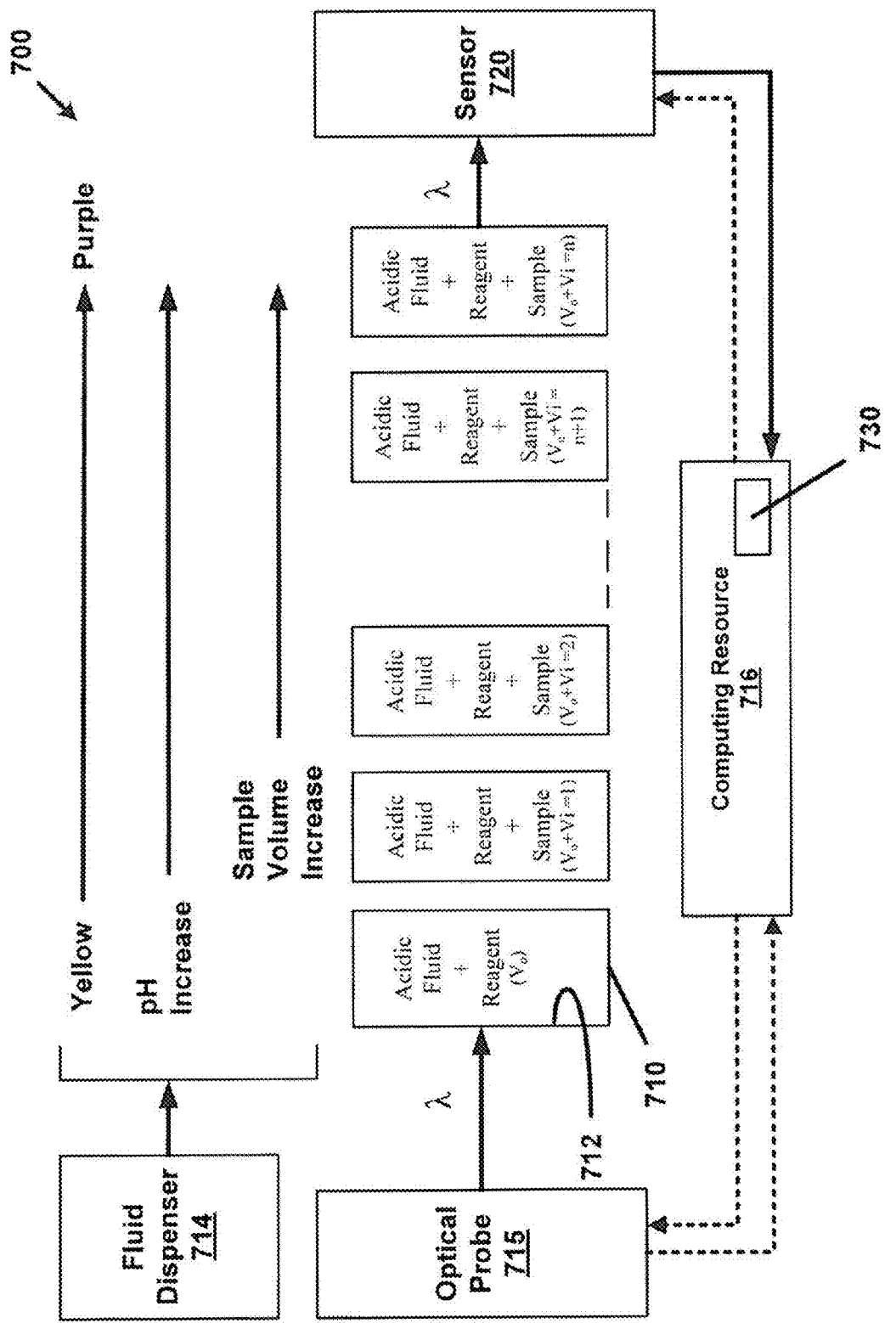
FIG. 7 illustrates an alkalinity determinator in accordance with embodiments.
Figure 8A:
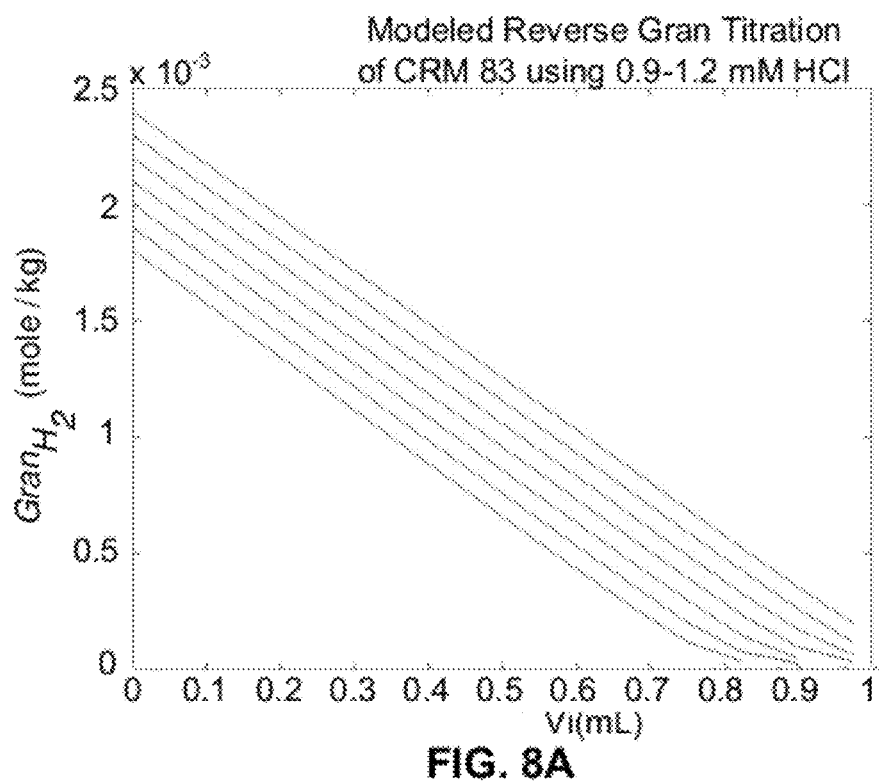
FIG. 8A to FIG. 8D are graphs illustrating an alkalinity determination process in accordance with embodiments.
Figure 8B:
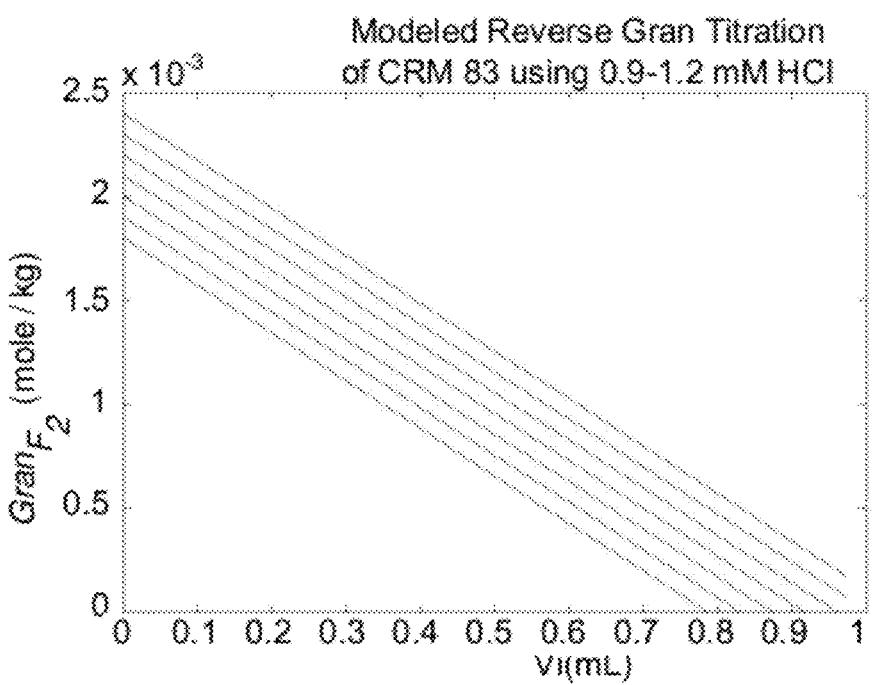
Figure 8C:
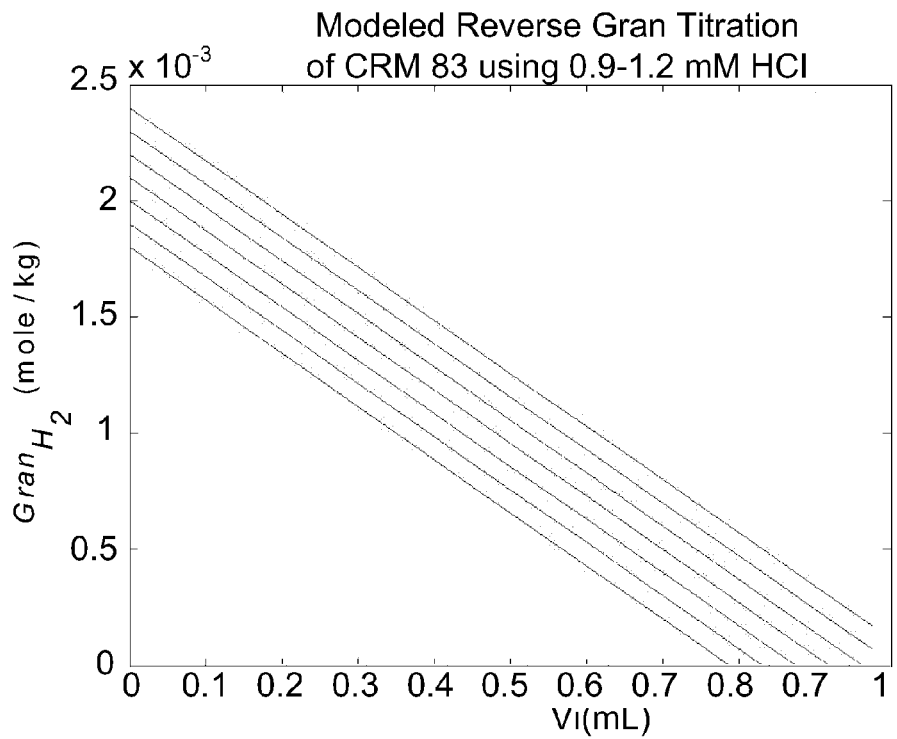
Figure 8D:
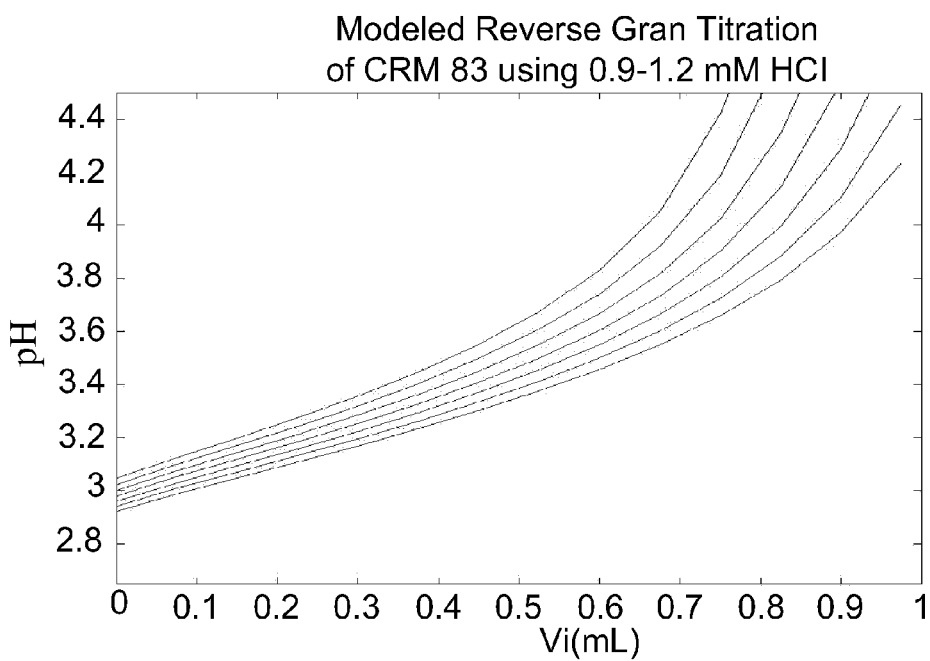

Referring to example FIG. 7, alkalinity determinator 700 may include one or more of a titration cell 710, fluid dispenser 714, sensor 720 and/or alkalinity value determinator 730. In embodiments, titration cells 710 may include chamber 712, which may be exposed to ambient conditions and/or may house one or more acidic fluids. In embodiments, chamber 712 may be in communication with sensor 720, for example through optical probe 715. In embodiments, alkalinity determinator 700 may include one or more fluid dispensers 714, which may be configured to supply alkaline fluid and/or may include a pipetter to be managed, for example, by pressure.

According to embodiments, titration cell 710 may house a reagent. In embodiments, a reagent may be provided to titration cell 710 by the same and/or similar dispensers described above, alone or in combination with acidic and/or alkaline fluids. In embodiments, a determined amount may include a predetermined amount and/or a measured amount. In embodiments, alkalinity determinator 700 may be configured to maintain the temperature of the titration system substantially constant, such that temperature may be determined by knowing a preselected value. In embodiments, a pH value may be inductively quantified using one or more measured absorbance values. In embodiments, an absorbance value may include values measured for a plurality of titration measurements, and/or a plurality of measurements for a single titration point, for example $\lambda$ at approximately 497, 434 and/or 512 nm.

According to embodiments, mixing may be achieved by any suitable operation, including providing a jet and/or a stirbar in titration cells 710, applying a force to a sidewall of titration cells 710 and/or by inducing and/or allowing motion for titration cells 710. In embodiments, mixing may be accomplished prior, during and/or after one or more additions of alkaline fluid.

According to embodiments, alkalinity value determinator 730 may be configured to determine an alkalinity value by calculating a transformation including one or more determined values. In embodiments, alkalinity value determinator 730 may be configured to utilize a determined pH value and/or a determined temperature value. In embodiments, alkalinity value determinator 730 may reside in computing resource 716. In embodiments, computing resource 716 may be in communication with titration cells 710, fluid dispenser 714, optical probe 715 and/or sensor 720.

According to embodiments, an alkalinity determination process may include modeling applications, such that an informed determination may be made with reference to relevant and/or irrelevant factors for a given system, as well as parameters to maximize likelihood of alkalinity determination. In embodiments, the influence of components of a system may be determined by employing processes and/or determinators in accordance with embodiments. In embodiments, parameters including pH, temperature, and/or components may be selected based on a modeling application. In embodiments, such selection may maximize real-time applications, for example when there is a relatively small amount of sample available and/or provide an maximized likelihood of alkalinity determination.

In embodiments, for example when a sample includes seawater, an influence of $A_T$, T, S, $C_T$, $C_a$, $P_T$ and/or $Si_T$ on a sample may be investigated. In embodiments, in one aspect, one or more of example equations (34)-(36) may be as follows:

$$A_{Ti} = \frac{V_i A_{Tsw} - V_O C_a}{(V_i + V_O)} \quad (34)$$

$$[H^+]_{Fi} = [HCO_3^-]_i + 2[CO_3^{2-}]_i + [B(OH)_4^-]_i + \\ [OH^-]_i + [HPO_4^{2-}]_i + 2[PO_4^{3-}]_i + [SiO(OH)_3^-]_i - \\ [HSO_4^-]_i - [HF]_i - [H_3PO_4]_i - \frac{V_i A_{Tsw} - V_O C_a}{(V_i + V_O)} \quad (35)$$

$$[H^+]_i = \frac{ZV_i \begin{pmatrix} [HCO_3]_{sw} + 2[CO_3^{2-}]_{sw} + \\ [B(OH)_4^-]_{sw} + [OH^-]_{sw} + [HPO_4^{2-}]_{sw} + \\ 2[PO_4^{3-}]_{sw} + [SiO(OH)_3^-]_{sw} - \\ [HSO_4^-]_{sw} - [HF]_{sw} - [H_3PO_4]_{sw} - A_{Tsw} \end{pmatrix} - V_O C_a}{(V_i + V_O)} \quad (36)$$

According to embodiments, $[H^+]_i$ may be inductively quantified using equations provided above, for example at each titration step $V_i$. In embodiments, equilibrium constants $K_{1C}$, $K_{2C}$, $K_B$, $K_W$, $K_{1P}$, $K_{2P}$, $K_{3P}$, $K_{Si}$, $K_S$, $K_F$ may be inductively quantified using related equations. In embodiments, total boron, fluorine, and sulfur may be assumed conservative and/or estimated using related salinity relationships. In embodiments, a series of equations inductively quantifying $[H^+]_i$ at each titration step may be solved using non-linear iterative solution routines in, for example, MATLAB® (Mathworks). In embodiments, modeling in accordance with embodiments may allow a user to input single values and/or ranges of T, S, $A_T$, $C_T$, $P_T$, and $Si_T$ to inductively quantify titration data.

EXAMPLE 1

Embodiment Electrochemical Operation

In operation, alkalinity determinator 600 may determine an alkalinity value. According to embodiments, standardized 1 M Hydrochloric acid may be diluted to approximately 0.62 mM using approximately 0.7 M KCl solution. In embodiments, sample including approximately 40 ml of Gulf Stream and/or Bahama water may be collected and stored for use, for example using approximately 10 μl $HgCl_2$. In embodiments, certified reference material may be used for one or more constituents in a sample. In embodiments, certified reference material for $CO_2$ in seawater may be available from the A. Dickson laboratory at Scripps Institute of Oceanography.

According to embodiments, disposable 20 ml plastic vials may be used as open titration cells. In embodiments, a laboratory benchtop pH meter (Mettler-Toledo SevenMulti™ S80), with combination micro pH probe (InLab® Micro) and automatic temperature correction (ATC, 30K NTC) may be used to measure pH and/or temperature for a titration. In embodiments, two digital burettes (Hirschm Solarus) with ±5 μl precision may add acidic fluid and seawater to titration cell 610. In embodiments, a titration system may be mixed with a teflon-coated magnetic stirbar 619 for approximately 10 s after each addition.

According to embodiments, a pH electrode may be calibrated prior to determination. In embodiments, a volume of an initial approximate 10 ml of acidic fluid, for example 0.62 mM HCl provided in a titrant cell, may be measured. In embodiments, a pH and/or a temperature of an initial acidic fluid volume may be measured using a benchtop pH meter with ATC. In embodiments, approximately 100 μl seawater may be added using digital buret 614, and an actual added volume may be recorded. In embodiments, mixing and/or stabilization of a pH measurement for approximately 30 s may be included, and/or pH and/or temperature of a titration system including the acidic fluid and seawater may be measured and/or recorded. In embodiments, a boundary pH value of approximately 4.5 may terminate a further addition of the alkaline fluid.

According to embodiments, a first-order polynomial least squares regression of a first data subset from initial acidic fluid with 0 ml seawater to a final solution of pH approximately 3.2 using equation (26) may be determined. In embodiments, $C_a$ may be inductively quantified as described above. In embodiments, a first-order polynomial least squares regression of a second titration subset of data from a pH of approximately 3.2 to a pH of approximately 3.6 using equation (26) and fixing the y-intercept using example equation (33) may be determined. In embodiments, the initial total alkalinity of the seawater may be directly correlated to the negative slope of the relation. In embodiments, a priori knowledge of total constituents, for example of carbon ($C_T$) and/or total phosphorous ($P_T$) may not be needed.

According to embodiments, equations (25) and/or (27) may be utilized depending on the selected constituents and/or knowledge of selected constituents. In embodiments, for example, $C_T$ may be inductively quantified for equation (25) and/or $C_T$ and $P_T$ may be inductively quantified for equation (27). In embodiments, a first-order polynomial least squares regression of a first data subset from initial acidic fluid with 0 ml seawater to a final solution of pH approximately 3.2 using equation (26) may be determined. In embodiments, $C_a$ may be inductively quantified as described above. In embodiments, a first-order polynomial least squares regression of a second titration subset of data from a pH of approximately 3.2 to a pH of approximately 4.5 using equations (25) and/or (27), while fixing the y-intercept using example equation (33), may be determined. In embodiments, the initial total alkalinity of the seawater may be directly correlated to the negative slope of the relation.

EXAMPLE 2

Embodiments Spectrophotometric

In operation, alkalinity determinator 700 may determine an alkalinity value. According to embodiments, Bromophenol Blue (BPB) may be dissolved in deionized water, for example to make an approximate 0.20 M stock indicator solution. In embodiments, approximately 1 M Hydrochloric acid may be diluted to approximately 0.62 mM using deionized water. In embodiments, approximately 1 mL of BPB stock solution may be added to 1 L of acid reagent. In embodiments, subsequent 0.20 mM BPB-indicator-acid-reagent solution may provide a concentration for 1-cm path length spectrophotometric determination of solution pH. In embodiments, sample including approximately 40 ml of Gulf Stream and/or Bahama water may be collected and stored for use, for example using approximately 10 μl $HgCl_2$. In embodiments, certified reference material for CO, in seawater may be available from the A. Dickson laboratory at Scripps Institute of Oceanography.

According to embodiments, disposable 2 ml polystyrene cuvettes may be used as open titration cells 710. In embodiments, six or more polystyrene 1-cm path length cuvettes may be initially inspected, wiped of debris and/or other visible obstruction on an optical cell wall. In embodiments, a Hach DR5000 scanning UV-Visible spectrophotometer with Peltier-temperature-controlled cuvette holder may be used to measure absorbance of a titration system. In embodiments, volumes of one or more acidic fluids, reagents and/or alkaline fluids may be measured using an Eppendorf Xs Multi-pipetter. In embodiments, a new disposable tip may be used to add seawater sample of increasing analytical volume, for example between approximately 75 μl and 325 μl, to all but one of polystyrene cuvettes, which may be used as a control. In embodiments, substantially the same volume, for example approximately 2 ml of acid reagent-pH indicator mixture, may be provided to all cuvettes. The relatively large volume of acid reagent to seawater sample may provide maximized mixing.

According to embodiments, each reaction solution may reference individual steps in a reverse Gran titration procedure. In embodiments, each reaction solution may be measured for visible light absorbance between approximately 330 nm and 730 nm. In embodiments, BPB peak absorbance may center on approximately 485 nm and 510 nm. In embodiments, slight shifts in peak absorbance frequencies may occur when temperature changes. In embodiments, the isosbestic point for BPB may be at approximately 497 nm. In embodiments, background measurement and comparison among all cuvettes may be accomplished in a non-absorbing region between approximately 720 nm and 730 nm. In embodiments, multiple points may provide a maximized determination of background changes among different cuvettes.

According to embodiments, BB may be added to excess strong acidic fluid producing acidic yellow color. In embodiments, as seawater sample $V_i$ is added illustrated in one aspect of embodiments in FIG. 7 to separate spectrophotometric cuvettes each starting with substantially the same initial acid volume $V_o$, pH increases and changes the BB indicator color to a purple, basic endpoint. In embodiments, pH may be inductively quantified as it increases in proportion to volume added and sample alkalinity. As discussed above, an alkalinity value may be determined by calculating a transformation comprising at least one of the at least one determined value.

EXAMPLE 3

Embodiment Modeling Applications

According to embodiments, a titration model may be manipulated to incorporate random Gaussian errors in components, for example, $T_i$, $S_{SW}$, Ca, pH, $V_o$, and/or $V_i$ measurements. In embodiments, analysis of titrations may, for example, estimate operational precision and/or accuracy of processes and/or determinators. In embodiments, subsets of modeled Monte Carlo titration data may be utilized in calculations of $C_a$, $A_T$, and $C_T$ using varying starting and ending points of individual data sets. In embodiments, values of $C_a$, $A_T$, and $C_T$ determined from such data may be normalized to a modeled data for accuracy comparison among varied conditions. In embodiments, a standard deviation of normalized response may provide an indication of process precision.

According to embodiments, process maximization may include a subset of data, for example pH and/or volume data from a titration curve, to determine a factor which may be important to a particular system of interest. Example FIG. 8A to FIG. 8D illustrate one aspect of embodiments of mass balance and/or pH modeling.

According to embodiments, for example, a starting point of a data subset may include an initial seawater volume. In embodiments, an ending point of a data subset may include a pH value. In embodiments, example Table 1 (example FIG. 9) may reference one aspect of embodiments of a normalized response of $C_a$ when varying starting volume and ending pH. In embodiments, a maximized starting point of data subset may be $V_i$ at approximately 0, while a maximized ending may be at pH at approximately 3.3. In embodiments, $1^{st}$ order polynomial least-squares regression, $2^{nd}$ and/or $3^{rd}$ order polynomial least-squares regressions may be utilized, where $1^{st}$ order polynomial least-squares regression may provide maximum precision.

According to embodiments, Monte Carlo modeled data may predict precision base on volume, pH, salinity, temperature, $C_T$, and/or $P_T$ measurements. In embodiments, for example, normalized accuracy and precision, utilizing data from pH at approximately 3.2 and pH at approximately 4.2, with measured sample $C_T$ and $P_T$, may be at approximately 0.9998±0.0012. In embodiments, for example, a measurement of 2199.6±2.6 μeq kg$^{-1}$ on a sample with 2200 μeq kg$^{-1}$ $A_T$, accuracy within 0.5 μeg kg$^{-1}$ and precision <3 μeq kg$^{-1}$ may be achieved. In embodiments, initial $A_T$, without $C_T$ and/or $P_T$ data and using 3 points between a pH of approximately 3.2 and 3.6 may prove useful for relatively fast field-based measurements that may have limited ancillary data. In embodiments, normalized accuracy and precision estimated from such models may be approximately 0.9986±0.0250, 2197±55 μeg kg$^{-1}$ on a 2200 μeg kg$^{-1}$ sample. In embodiments, processes may utilize substantially all points to estimate acid analyte concentration, not just data at a pH below approximately 3.3. In embodiments, pH calibration, both using NBS standards to determine an electrode response slope, s, and/or in high-ionic-strength solution to determine $E°_{(KCl)}$ may be useful.

EXAMPLE 4

Further Non-Limiting Embodiments

According to embodiments, an alkalinity determinator may be portable. In embodiments, for example, alkalinity determinator 400 may include an enclosed and mobile titration cell 410, sensor 420, and/or alkalinity value determinator

430. In embodiments, alkalinity determinator 400 may be deployed into a system of interest and alkaline fluid may be added to titration cell in accordance with one or more embodiments described provided above, for example using an electronic controller to actuate a valve for fluid flow.

According to embodiments, alkalinity determinator 430 may operate by admitting one or more alkaline fluid additions to titration cell 410 while floating on a system of interest, as it descends to a predetermined and/or random depth, as it emerges from a depth, and/or while submerged. In embodiments, alkaline fluid additions may occur at predetermined and/or random intervals, for example based on pressure, depth, temperature, time and/or atmospheric conditions.

According to embodiments, mixing may be included as described above, for example through jets configured to provide turbulent flow. In embodiments, alkalinity value determinator 430 may be in communication with computing resource 416, which may reside in alkalinity determinator 400 and/or may collect data for storage, for transmission, buffering, and/or any other suitable operation to determine alkalinity.

Alkalinity determination in accordance with embodiments may achieve maximized precision and/or accuracy, for example precision between approximately ±3 $\mu$eg kg$^{-1}$ and ±55 $\mu$eq kg$^{-1}$ and/or accuracy between approximately ±0.5 $\mu$eq kg$^{-1}$ and ±3 $\mu$eq kg$^{-1}$. In embodiments, minimized sample size may be used, for example between approximately 1 ml and 5 ml, such that relatively high quality alkalinity measurements may be achieved where sample size may be limited, for example under microfluidic conditions including in pore waters.

Alkalinity determination in accordance with embodiments may not require accurate and/or frequent calibration of acid titrant, for example HCL which may be relatively difficult to calibrate and may not be stable. In embodiments, alkalinity determination may be achieved using inexpensive and/or readily available devices, for example as pH meters, burets, and spectrophotometers. In embodiments, special closed-titration cells with 5-6 significant digit high-impedance voltmeters may be unnecessary. In embodiments, the time to complete alkalinity determination may be minimized, for example less than approximately 10 minutes for a determination.

Alkalinity determination in accordance with embodiments may not require a priori knowledge of total constituents, for example of carbon ($C_T$) and/or total phosphorous ($P_T$). In embodiments, a pH range, for example approximately between 3.2 and 3.6, may be used such that [$HCO_3^-$], [$HPO_4^{2-}$], and [$H_3PO_4$] may be 1-2 orders of magnitude lower than [$HSO_4$] and/or [HF], which may be primary constituents influencing $A_T$ at a particular pH. In embodiments, in an acidic pH of a titration, [$SiO(OH)_3^-$] may be several orders of magnitude lower than even [$HCO_3^-$], and may be ignored.

Alkalinity determination in accordance with embodiments is versatile. In embodiments, constituents may vary, for example even seawater constituents may naturally vary. According to embodiments, if $C_T$ and $P_T$ data are available, incorporation into $F_2$ and/or $I_2$ calculations may provide maximized precision. In embodiments, random errors in pH and/or buret volume measurements may cancel, improving an overall process precision. In embodiments, a relatively large data set may provide maximized confidence in a linear regression to determine $A_T$, although process may determine alkalinity with a single addition.

According to embodiments, instructions developed, including Matlab® (Mathworks®) routines, coupled with automated data recordings, including from pH meters, may facilitate real-time $A_T$ calculations and/or an ability to investigate individual systems to determine relevant and/or irrelevant factors, such as pH, temperature, constituents, and the like. In embodiments, non-linear data fitting and/or relatively complex, multi-variate iterative solutions may not be needed. In embodiments, relative ease of data collection and/or straight-forward calculations show titrations may be automated for unattended relatively high-precision analytical $A_T$ measurements. In embodiments, relatively high quality electrochemical pH measurements and/or spectrophotometric techniques may offer relatively high precision and/or accuracy of measurements, and/or complications associated with high-ionic-strength solutions and/or temperature sensitivity may be addressed.

Many of the elements described in the disclosed embodiments may be implemented as modules. A module is defined here as an isolatable element that performs a defined function and has a defined interface to other elements. The modules described in this disclosure may be implemented in hardware, software, firmware, wetware (i.e hardware with a biological element) or a combination thereof, all of which are behaviorally equivalent. For example, modules may be implemented as a software routine written in a computer language (such as C, C++, Fortran, Java, Basic, Matlab or the like) or a modeling/simulation program such as Simulink, Stateflow, GNU Octave, or LabVIEW MathScript. Additionally, it may be possible to implement modules using physical hardware that incorporates discrete or programmable analog, digital and/or quantum hardware. Examples of programmable hardware include: computers, microcontrollers, microprocessors, application-specific integrated circuits (ASICs); field programmable gate arrays (FPGAs); and complex programmable logic devices (CPLDs). Computers, microcontrollers and microprocessors are programmed using languages such as assembly, C, C++ or the like. FPGAs, ASICs and CPLDs are often programmed using hardware description languages (HDL) such as VHSIC hardware description language (VHDL) or Verilog that configure connections between internal hardware modules with lesser functionality on a programmable device. Finally, it needs to be emphasized that the above mentioned technologies are often used in combination to achieve the result of a functional module.

The disclosure of this patent document incorporates material which is subject to copyright protection. The copyright owner has no objection to the facsimile reproduction by anyone of the patent document or the patent disclosure, as it appears in the Patent and Trademark Office patent file or records, for the limited purposes required by law, but otherwise reserves all copyright rights whatsoever.

While various embodiments have been described above, it should be understood that they have been presented by way of example, and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments. Thus, the present embodiments should not be limited by any of the above described exemplary embodiments. In particular, it should be noted that, for example purposes, the above explanation has focused on the example(s) related to fluids such as seawater. However, one skilled in the art will recognize that embodiments could be applied to any relatively alkaline fluid added to a relatively acidic fluid. In embodiments, for example, bodily fluid including a carbonate system such as blood may be used. Embodiments may also recognize other constituents than those provided above, for example bisulfide ion HS$^-$, SiO(OH)$_3^-$, ammonia NH$_3$, and any other constituent of any chemical reaction of interest. It should also be noted that one skilled in the art will recognize that alkalinity determination may use an example equation of the general form as follows:

$$X_2 = (V_t + V_o)([Proton]_{system}) + V_t([Y]_{sample}\ldots) \quad (37)$$

where $X_2$ represents a mass balance, Y includes a selected constituent of an alkaline sample, and . . . represents optional constituents which may be included. While Y sample may be relatively difficult to determine, conservative mixing constituents, for example total S; total F, total C in seawater, may be utilized in accordance with aspects of embodiments.

In addition, it should be understood that any figures which highlight the functionality and advantages, are presented for example purposes only. The disclosed architecture is sufficiently flexible and configurable, such that it may be utilized in ways other than that shown. For example, the steps listed in any flowchart may be re-ordered or only optionally used in some embodiments.

Further, the purpose of the Abstract of the Disclosure is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract of the Disclosure is not intended to be limiting as to the scope in any way.

Finally, it is the applicant's intent that only claims that include the express language "means for" or "step for" be interpreted under 35 U.S.C. 112, paragraph 6. Claims that do not expressly include the phrase "means for" or "step for" are not to be interpreted under 35 U.S.C. 112, paragraph 6.

What is claimed is:

1. An alkalinity determination process comprising:
   a. providing a known amount of an acidic fluid at a pH value of approximately 4.5 or less;
   b. forming a titration system by providing at least one addition of a known amount of a seawater sample to the acidic fluid;
   c. determining at least one of a pH value and a temperature value for the at least one addition; and
   d. determining an alkalinity value of the sample comprising calculating a transformation irrespective of crossing the equivalence point of the system, including:
      i. incorporating a value of the amount of the at least one addition to an inductively quantified value of at least one of a hydrogen ion, a hydrogen sulfate ion, a hydrogen fluoride ion, a bicarbonate ion, a trihydrogen phosphate ion and a hydrogen phosphate ion in the seawater; and
      ii. at least one of the pH value and the temperature value of the at least one addition.

2. The alkalinity determination process of claim 1, comprising:
   a. inductively quantifying an acid concentration value of the acidic fluid; and
   b. using the inductively quantified acid concentration value as a limit to determine the alkalinity value.

3. The alkalinity determination process of claim 1, comprising measuring an initial pH value and an initial temperature value of the acidic fluid.

4. The alkalinity determination process of claim 1, comprising mixing for at least one of the at least one addition.

5. The alkalinity determination process of claim 1, wherein the value of the amount of at least one of the acidic fluid and the seawater is known by at least one of measuring and selection.

6. The alkalinity determination process of claim 1, comprising at least one of:
   a. an electrochemical operation; and
   b. a spectrophotometric operation.

7. The alkalinity determination process of claim 6, comprising at least one of:
   a. measuring the pH value and the temperature value for the electrochemical operation; and
   b. determining the temperature value for the spectrophotometric operation by keeping the temperature of the system substantially constant and inductively quantifying the pH value using at least one measured absorbance value.

8. An alkalinity determination process comprising:
   a. providing a known amount of an acidic fluid;
   b. forming a titration system by providing at least one addition of a known amount of a relatively alkaline fluid sample to the acidic fluid;
   c. determining at least one of a pH value and a temperature value for the at least one addition; and
   d. determining an alkalinity value of the sample by calculating a transformation irrespective of crossing the equivalence point of the system comprising at least one of the determined pH value and the temperature value of the at least one addition.

9. The alkalinity determination process of claim 8, wherein the alkaline fluid comprises at least one of:
   a. seawater;
   b. waste water;
   c. ground water;
   d. agricultural water;
   e. recreational water;
   f. industrial water; and
   g. drinking water.

10. The alkalinity determination process of claim 9, comprising a boundary pH value of approximately 4.5 which terminates a further addition of the at least one addition.

11. The alkalinity determination process of claim 8, wherein calculating the transformation comprises inductively quantifying a value of the number of protons in the system.

12. The alkalinity determination process of claim 1, wherein calculating the transformation comprises incorporating a value of the amount of the at least one addition to an inductively quantified value of a selected ion in the alkaline fluid.

13. The alkalinity determination process of claim 12, wherein the ion comprises at least one of:
   a. a hydrogen ion;
   b. a hydrogen sulfate ion;
   c. a hydrogen fluoride ion;
   d. a bicarbonate ion;
   e. a trihydrogen phosphate ion; and
   f. a hydrogen phosphate ion.

14. An alkalinity determinator comprising:
   a. at least one titration cell configured to house a titration system including:
      i. an acidic fluid; and
      ii. at least one added known amount of a relatively alkaline fluid sample to the acidic fluid;
   b. at least one sensor configured to determine at least one of:
      i. at least one pH value of the system for at least one of the at least one added known amount;
      ii. at least one temperature value of the system for at least one of the at least one added known amount; and
      iii. at least one absorbance value of the system for at least one of the at least one added known amount; and
   c. at least one alkalinity value determinator, wherein an alkalinity value is determined by calculating a transformation irrespective of crossing the equivalence point of the system and comprising at least one of the at least one determined values.

15. The alkalinity determinator of claim 14, comprising:
 a. a chamber configured to house at least the acidic fluid in communication with the sensor; and
 b. at least one alkaline fluid dispenser in communication with the chamber.

16. The alkalinity determinator of claim 15, wherein at least one of:
 a. the dispenser comprises at least one of:
  i. a buret including at least one of a pump and a valve; and
  ii. a pipetter,
  iii. wherein at least one of the buret and the pipetter is configured to be managed by at least one of an electronic controller and pressure; and
 b. at least one of the sensor and the dispenser is configured to communicate with a computing resource, the computing resource configured to implement at least one of storing, processing and outputting data.

17. The alkalinity determinator of claim 16, wherein at least one of the buret and the pipetter is configured to dispense the alkaline fluid from a source to the chamber by at least one of:
 a. a predetermined amount; and
 b. a measured amount.

18. The alkalinity determinator of claim 14, wherein the sensor is configured to measure the at least one of the at least one pH value, temperature value and absorbance value.

19. The alkalinity determinator of claim 14, wherein:
 a. the chamber houses a reagent;
 b. the sensor is configured to maintain the temperature of the system substantially constant; and
 c. the pH value is inductively quantified by measuring the absorbance value.

20. The alkalinity determinator of claim 14, wherein calculating the transformation comprises incorporating a value of the amount of the at least one addition to an inductively quantified value of a selected ion in the alkaline fluid.

21. The alkalinity determination process of claim 8, wherein the transformation is represented as a function having a slope value at least approximating the alkalinity value of the relatively alkaline fluid sample.

22. The alkalinity determination process of claim 21, wherein the function comprises the derivative of a mass balance of the selected ion with respect to the value of the amount of the at least one addition of the relatively alkaline fluid sample.

23. The alkalinity determination process of claim 8, wherein the transformation is representative of alkalinity added to the system by at least one of the at least one addition of the relatively alkaline fluid.

* * * * *